United States Patent
Gronau et al.

(10) Patent No.: US 9,950,104 B2
(45) Date of Patent: Apr. 24, 2018

(54) METHOD FOR RINSING AND/OR FOR FILLING A BLOOD TREATMENT DEVICE AND BLOOD TREATMENT DEVICE

(75) Inventors: Soeren Gronau, Nauheim (DE); Joachim Noack, Bad Neustadt (DE); Juergen Haecker, Neu-Anspach (DE); Ralf Mueller, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 738 days.

(21) Appl. No.: 13/477,562

(22) Filed: May 22, 2012

(65) Prior Publication Data
US 2012/0298580 A1 Nov. 29, 2012

Related U.S. Application Data

(60) Provisional application No. 61/457,740, filed on May 24, 2011.

(30) Foreign Application Priority Data

May 24, 2011 (DE) .................. 10 2011 102 492

(51) Int. Cl.
*B01D 11/00* (2006.01)
*B01D 61/00* (2006.01)
(Continued)

(52) U.S. Cl.
CPC ............ *A61M 1/3643* (2013.01); *A61M 1/16* (2013.01); *A61M 1/365* (2014.02); *A61M 1/3644* (2014.02); *A61M 2205/14* (2013.01)

(58) Field of Classification Search
CPC ...... A61M 1/16; A61M 1/165; A61M 1/1656; A61M 1/30; A61M 1/302; A61M 1/303;
(Continued)

(56) References Cited

U.S. PATENT DOCUMENTS 4,618,343 A 10/1986 Polaschegg
5,770,064 A 6/1998 Jönsson et al.
(Continued)

FOREIGN PATENT DOCUMENTS

CN 101443057 5/2009
CN 101868261 10/2010
(Continued)

OTHER PUBLICATIONS

A machine-translated EP1892000 Author: Stefan Moll Title: Method for priming the filter element of a dialysis machine Date: Aug 27, 2008.*
(Continued)

*Primary Examiner* — Dirk Bass
*Assistant Examiner* — Hayden Brewster
(74) *Attorney, Agent, or Firm* — Jacobson Holman, PLLC.

(57) ABSTRACT

A method of rinsing and/or filling a blood treatment device, in particular for priming a blood treatment device, is associated with a blood treatment device that includes a membrane filter, in particular a hollow fiber membrane filter, a first partial circuit, and a second partial circuit. The first and the second partial circuits are separated by the membrane filter in a semipermeable manner, with temporarily the first partial circuit being first filled with a fluid with a uniform and/or a pulsatile first volumetric flow rate, with the volumetric flow rate not exceeding a specified threshold value at which the fluid has not completely wetted and/or soaked the membrane. The second partial circuit is temporarily open towards the atmosphere, air is displaced from the first partial circuit into the second partial circuit via the membrane, and during filling no negative pressure is applied to the first partial circuit.

15 Claims, 2 Drawing Sheets

(51) Int. Cl.
    *C02F 1/44*     (2006.01)
    *A61M 1/16*    (2006.01)
    *A61M 1/36*    (2006.01)
    *B01D 63/00*   (2006.01)
    *C02F 9/00*     (2006.01)

(58) Field of Classification Search
    CPC ........ A61M 1/34; A61M 1/3427; A61M 1/36;
              A61M 1/365; A61M 1/3604; A61M
              1/3629; A61M 1/3643; A61M 1/3772;
              A61M 2001/3437; A61M 2205/14; A61M
              2209/088; B08B 3/04; B01D 11/00;
              B01D 13/01; B01D 21/30; B01D 29/42;
              B01D 35/147; B01D 35/153; B01D
              61/00; B01D 61/12; B01D 61/145; B01D
              61/18
    See application file for complete search history.

(56) References Cited

U.S. PATENT DOCUMENTS

| | | | |
|---|---|---|---|
| 5,776,345 A | 7/1998 | Truitt et al. | |
| 5,893,382 A | 4/1999 | Bardelli et al. | |
| 7,935,258 B2 | 5/2011 | Rovatti et al. | |
| 2004/0084371 A1* | 5/2004 | Kellam et al. | 210/646 |
| 2004/0149656 A1* | 8/2004 | Rovatti | A61M 1/168 |
| | | | 210/636 |
| 2005/0131332 A1* | 6/2005 | Kelly et al. | 604/4.01 |
| 2009/0076433 A1* | 3/2009 | Folden et al. | 604/4.01 |
| 2009/0114593 A1* | 5/2009 | Fischer | A61M 1/3643 |
| | | | 210/636 |
| 2010/0274168 A1* | 10/2010 | Gronau | A61M 1/30 |
| | | | 604/5.04 |
| 2015/0165109 A1 | 6/2015 | Fischer | |

FOREIGN PATENT DOCUMENTS

| | | | | |
|---|---|---|---|---|
| DE | 696 25 279 | 4/2003 | | |
| DE | 696 23 563 | 5/2003 | | |
| EP | 1 892 000 | 2/2008 | | |
| EP | 1892000 A1 * | 2/2008 | ............ | A61M 1/36 |
| JP | 60-068862 | 4/1985 | | |
| JP | S60150758 | 8/1985 | | |
| JP | 07-073605 | 3/1995 | | |
| JP | 07-328113 | 12/1995 | | |
| JP | 2607798 | 5/2002 | | |
| JP | 3499002 | 12/2003 | | |
| JP | 2007-510473 | 4/2007 | | |
| JP | 2007-167108 | 7/2007 | | |
| JP | 4101512 | 3/2008 | | |
| JP | 4387631 | 10/2009 | | |
| JP | 2010-000161 | 1/2010 | | |
| WO | WO 2004/043520 | 5/2004 | | |

OTHER PUBLICATIONS

EP1892000A1 Moll_English Translation from Transperfect (Feb. 27, 2008; 8 pages).*
EP1892000A1_Translation Certification.*

* cited by examiner

METHOD FOR RINSING AND/OR FOR FILLING A BLOOD TREATMENT DEVICE AND BLOOD TREATMENT DEVICE

CROSS-REFERENCE TO RELATED APPLICATIONS

This application claims the benefit of U.S. provisional application No. 61/457,740, filed May 24, 2011, which claims the priority of German number 10 2011 102 492.5 filed May 24, 2011, hereby incorporated by reference.

BACKGROUND OF THE INVENTION

1. Field of Invention

The present invention relates to a method for rinsing and/or for filling a blood treatment device and to a blood treatment device.

2. Description of the Prior Art

Before putting blood treatment devices, in particular dialysis machines into operation, it is required to correspondingly upgrade the machine for example before a dialysis treatment and to vent both the dialysis circuit, the extracorporeal blood circuit and the used membrane filter or dialysis filter. For this purpose, the dialysis circuit, the extracorporeal blood circuit and also the dialysis filter separating the dialysis circuit from the blood circuit in a semipermeable manner generally is rinsed.

To increase the efficiency of the purification of blood during the treatment of the blood, the blood flowing in the hollow fibers of the dialyzer flows in a direction opposite to the flow direction of the dialysis solution. The dialysis solution is located outside the hollow fibers of the dialyzer. As during the treatment the air on the blood side is regarded as more problematic than on the dialysate side, in particular because of possible air infusions which can lead to air embolisms, the dialyzers are arranged such that during the treatment the blood flows through the dialyzer from bottom to top, whereas the dialysis solution flows from top to bottom. For this reason, the removal of air on the dialysate side, in particular in large dialyzers, often is not optimal and collections of residual air, also recognizable for the user, regularly are left in the dialyzer, in particular on the dialysate side.

This fact is overcome in that the dialyzer is rotated by the operating personnel of the dialysis station, and by subsequently or simultaneously knocking on the dialyzer it is attempted to remove the residual air from the dialyzer. By rotating, the dialysate outlet is moved to the top, whereby residual air can be rinsed out of the dialyzer more easily. In this way, a good venting can be achieved on the dialysate side, in particular on the dialysate side of the dialyzer.

A disadvantage consists in that such rotating must be performed by the user manually and in a time-consuming manner, that on knocking the user possibly can damage the dialyzer and also higher costs are produced due to the fact that the dialyzer connection tubes of the tube system must be designed very long, in order to provide for rotating the dialyzer. At the same time, the extracorporeal blood volume thereby is increased in a disadvantageous way. In addition, the venting of the blood side with rotated filter is deteriorated, which is the case in particular when the dialyzer erroneously is not rotated back into the starting position, i.e. the blood inlet again is located at the lower end of the dialyzer and the dialysate inlet is located at the upper end of the dialyzer.

From the prior art, devices are known already by means of which rotating the dialyzer can be facilitated.

For example, DE 696 25 279 T2 discloses a dialysis machine which includes a dialyzer holder by means of which the dialyzer can automatically be rotated during filling.

Alternatively, there are already known methods by means of which the step of rotating the dialyzer should be avoided.

For example, DE 696 23 563 T3 discloses a method and an apparatus for rinsing a dialyzer, in which after filling the extracorporeal blood circuit pressure waves are generated in the rinsing circuit, so that adhering air bubbles should be released. At the same time, there is also described a circuit in which in the rinsing mode the blood and dialysate compartments are traversed from bottom to top.

WO 2004/43520 A1 describes a method in which the fibers of the filter first are filled by means of the blood pump from inside at a low pressure or flow rate and then are rinsed at a higher pressure. The dialysate then is pressed e.g. through the membrane into the dialysate space. There, it is pumped over by the dialysate pump for rinsing, wherein a reversal of direction also is possible in part. By rinsing at higher flow rates the air should be removed. According to WO 2004/43520 A1 filling of the hemodialyzer first is effected on the blood side by means of the blood pump. The priming solution is delivered by the blood pump into the interior of the hollow fibers and from there pressed through the membrane onto the dialysate side.

It would be desirable to provide for an automatic and safe filling of the dialysate side, the blood side and the dialyzer in blood treatment devices which employ membrane filters, as is the case for example in dialysis machines and dialyzers.

SUMMARY OF THE INVENTION

Therefore, it is the object of the present invention to develop a blood treatment device and a method as mentioned above in an advantageous way, in particular to the effect that the used filter can automatically be filled free from air, without further working steps having to be performed by the nursing staff.

In accordance with the invention, this object is solved by a method for rinsing and/or filling a blood treatment device with the features described herein. Accordingly it is provided that in a method for rinsing and/or filling a blood treatment device, wherein the blood treatment device includes at least one membrane filter, at least one first partial circuit and at least one second partial circuit, wherein the first and the second partial circuits are separated by the membrane filter in a semipermeable manner, the procedure is at least such that the first partial circuit is at least temporarily filled with a fluid with a uniform and/or a pulsatile first volumetric flow rate, wherein the volumetric flow rate does not exceed a specified threshold value, wherein at this threshold value the fluid has not yet completely wetted and/or soaked the membrane, and/or that the second partial circuit is at least temporarily open towards the atmosphere, and wherein air is displaced via the membrane of the membrane filter from the first into the second partial circuit and/or that during filling no negative pressure is applied to the first partial circuit. The first partial circuit is filled first, while the second partial circuit still is empty.

In particular, the rinsing and/or filling of the blood treatment device constitutes the priming of a blood treatment device. The membrane filter preferably is a hollow fiber membrane filter. This blood treatment device advantageously can be a dialysis machine. The fluid utilized for the filling operation or for the priming for example can be the dialysis fluid.

The removal of air from the membrane filter can be improved considerably without any mechanical manipulation of the membrane filter and without any technical changes of the blood treatment device. In particular, it is advantageous that the membrane filter now can be filled automatically and can safely be vented, without further working steps such as turning over the membrane filter having to be performed e.g. by the nursing staff. Particularly advantageously, it is possible to remove the air present in the first partial circuit via the membrane of the membrane filter during the filling phase of the membrane filter.

This is promoted in particular by the fact that by carefully filling the first partial circuit and the side of the membrane filter located on this side of the partial circuit with a volumetric flow rate below a specified threshold value, the membrane still remains quite permeable to air. By reducing the wetting and by reducing the soaking of the membrane of the membrane filter, it is achieved that the air can pass through the membrane comparatively unimpeded. Such unimpeded passage of air, however, no longer is easily possible when the membrane of the membrane filter is strongly wetted and/or soaked with fluid.

Furthermore, it is advantageous that the second partial circuit is at least temporarily open towards the atmosphere, as in this way it is achieved in particular that in the second partial circuit an only low back pressure exists when air should be displaced from the first partial circuit into the second partial circuit, as it is provided while air is displaced from the first into the second partial circuit via the membrane of the membrane filter. In this way, the air can easily be removed via the membrane.

Preferably and in particular in the working or treatment position, the membrane filter is arranged substantially vertically in or at the blood treatment device. The first and second partial circuits are arranged such that the flow directions through the membrane filter are in the opposite sense, i.e. the membrane filter is traversed in counterflow. During the filling operation, the fluid in the first partial circuit flows through the membrane filter from top to bottom on the corresponding side of the membrane filter and in the second partial circuit correspondingly in the opposite sense, i.e. through the membrane filter from bottom to top on the corresponding side of the membrane filter.

In the method of the invention, the occurrence of air bubbles in the first partial circuit thus is advantageously reduced by promoting the removal of air via the membrane. Already while filling the hollow fiber membrane filter with the small first volumetric flow rate, which does not exceed a threshold value, air is displaced via the membrane into the second partial circuit and from there e.g. into the surroundings.

By omitting the application of a negative pressure in the first partial circuit, it is effected that during the filling operation the hollow fiber membrane can remain permeable to air for a longer period and also no air can flow backwards from the second partial circuit into the first partial circuit, which would lead to the fact that the air can no longer be removed.

This is promoted in particular by the fact that alternatively or preferably combined by the first volumetric flow rate a slower wetting of the hollow fiber membrane surface is effected, furthermore by omitting the application of a negative pressure in the first partial circuit, a slower wetting of the hollow fiber membrane surface likewise is effected, and by opening the second partial circuit to the atmosphere it is achieved that no back pressure is built up, which promotes a faster wetting of the hollow fiber membrane surface.

In particular, it can be provided that the first partial circuit is the dialysis circuit and/or that the second partial circuit is the extracorporeal blood circuit.

Furthermore it is conceivable that the membrane filter first is filled in a balancing manner on the side of the first partial circuit, wherein during the balancing filling equal volumes are delivered to and from the membrane filter and wherein a balancing chamber is used for the balancing filling.

Furthermore it is possible that while filling the membrane filter on the side of the first partial circuit, one or more balancing chamber switching operations are effected.

It is particularly advantageous when preferably three balancing chamber switching operations are provided.

In addition, it can be provided that after a specified number of balancing chamber switching operations air is displaced from the first into the second partial circuit via the membrane of the membrane filter. It can thereby be avoided, for example, that the secondary air separator runs idle when in the blood treatment device to be filled the air from the first partial circuit first is delivered into a secondary air separator.

Furthermore, it can be provided that on the side of the first partial circuit the membrane filter is filled with a first volumetric flow rate which does not exceed about 500 ml/min. By means of this reduced and uniform volumetric flow rate of the fluid with which the first partial circuit is filled and with which also the first side of the membrane filter associated to the first partial circuit is filled, it is achieved that the membrane of the membrane filter is not completely drenched or soaked on this side. Thus, it can particularly advantageously be ensured that even despite the filling a passage of air via the membrane still is possible in an unproblematic manner.

Furthermore, it can be provided that the blood treatment device includes a secondary air separator into which the air from the membrane filter is delivered while filling the membrane filter on the side of the first partial circuit.

In addition, it can be provided that air from the secondary air separator and from the first partial circuit is displaced into the second partial circuit via the semipermeable membrane of the membrane filter.

Furthermore, it is conceivable that while air is displaced from the first into the second partial circuit via the membrane of the membrane filter, fluid is delivered into the first partial circuit with a volumetric flow rate which is greater than the first volumetric flow rate.

It is particularly advantageous when delivery is made with a volumetric flow rate of about 1300 ml/min. For this purpose, for example a charge pump of the blood treatment device can be used.

Furthermore, the present invention relates to a blood treatment device with the features described herein. Accordingly, it is provided that the blood treatment device is provided with at least one membrane filter, with at least one first partial circuit and with at least one second partial circuit, with at least one first pumping means for delivering a fluid in the first partial circuit and with at least one second pumping means for delivering a fluid in the second partial circuit, wherein the first and the second partial circuits are separated by the membrane filter in a semipermeable manner, wherein the blood treatment device includes at least one control and/or regulating means, so that the blood treatment device at least is operable such that by means of separate pumping means at least the first and the second partial circuit and the membrane filter can directly and/or indirectly be rinsed and/or filled, wherein at least temporarily the first partial circuit can be filled with a fluid with a uniform and/or a pulsatile volumetric flow rate, wherein the volumetric flow rate does not exceed a specified threshold value, wherein at this threshold value the fluid has not yet completely wetted and/or soaked the membrane, and/or wherein the second partial circuit is at least temporarily open towards the atmosphere and wherein air can be displaced from the first into the second partial circuit via the membrane of the membrane filter and/or wherein the blood treatment device is formed such that during filling no negative pressure is applied to the first partial circuit.

In addition, it can be provided that the blood treatment device is a dialysis machine and/or that the membrane filter is a hollow fiber membrane filter, in particular a dialyzer, and/or that the first partial circuit is the dialysis circuit and/or that the second partial circuit is the extracorporeal blood circuit.

Furthermore it is possible that the venting means, by means of which the second partial circuit can be vented towards the surroundings and/or the atmosphere and/or by means of which the second partial circuit can be opened towards the surroundings and/or the atmosphere, is and/or comprises a clamp element and/or an element comprising a hydrophobic membrane and/or a valve, wherein preferably the valve is a vent valve and/or a valve which is designed such that it increases the compliance of a disposable tubing set of the blood treatment device, in particular is a single-needle valve. The clamp element for example can be a tubing part of the disposable, which is provided with a manual clamp, whereby the disposable can be opened and closed towards the atmosphere.

It can also be provided that the blood treatment device includes at least one balancing chamber by means of which the first partial circuit can directly and/or indirectly be filled in a balancing manner.

Furthermore, it can be provided that the blood treatment device is configured and designed such that the membrane filter first is filled in a balancing manner on the side of the first partial circuit, wherein during the balancing filling equal volumes can be delivered to and from the membrane filter by means of the first pumping means and by means of the balancing chamber.

In addition, it is conceivable that on the side of the first partial circuit the membrane filter is filled by means of the first pumping means with a volumetric flow rate which does not exceed about 500 ml/min.

Furthermore, it is conceivable that the blood treatment device includes a secondary air separator into which the air from the membrane filter can be delivered while filling the membrane filter on the side of the first partial circuit.

In addition, it can be provided that by means of the blood treatment device the method described herein can be performed.

DETAILED DESCRIPTION OF THE PREFERRED EMBODIMENTS

Further details and advantages of the invention will now be explained in detail with reference to an exemplary embodiment.

The filling method of the invention preferably is performed with a blood treatment machine according to the invention, which is a dialysis machine or a dialysis monitor, wherein the first partial circuit is the dialysate circuit and the second partial circuit is the extracorporeal blood circuit.

Figure 1:
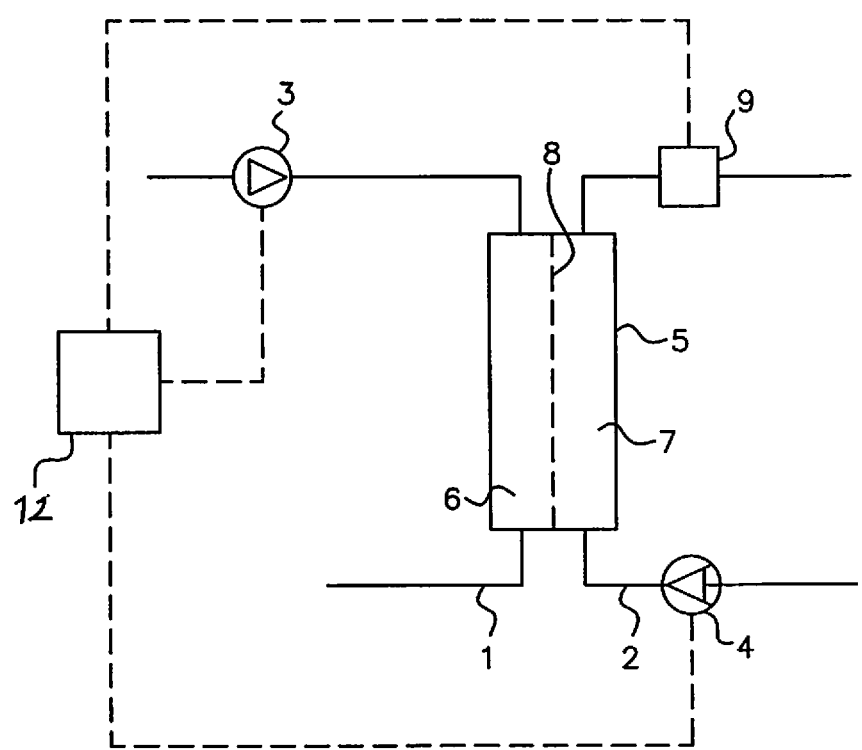
FIG. 1 illustrates a blood treatment device according to one embodiment of the present invention.

As shown in FIG. 1, the blood treatment device includes a first partial circuit 1, a second partial circuit 2, a first pump 3, a second pump 4, a membrane filter 5, a dialysis compartment 6 of the membrane filter, a blood compartment 7 of the membrane filter, a semipermeable membrane 8, an opening/vacuum/vent 9, and a controller 12.

Figure 2:
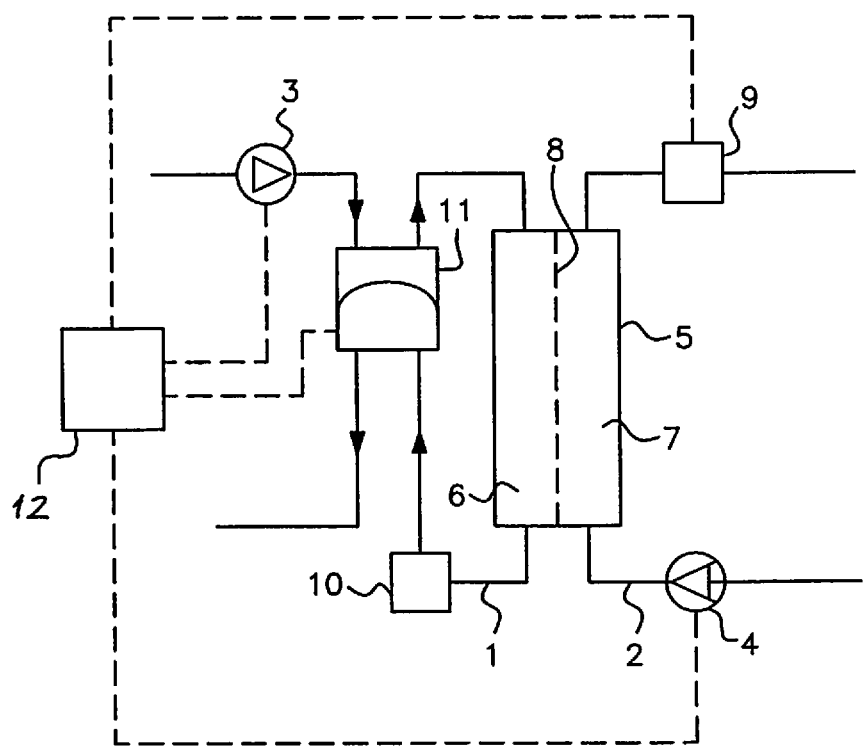
FIG. 2 illustrates a blood treatment device according to another embodiment of the present invention.

As shown in FIG. 2, according to another embodiment of the present invention, the blood treatment device also includes a secondary air separator 10, and a balancing chamber 11.

When filling or priming the first and second partial circuits as well as the dialyzer, the fact is utilized that by carefully filling the first partial circuit and the side of the membrane filter located on this side of the partial circuit with a volumetric flow rate below a specified threshold value, the membrane still remains quite permeable to air. By reducing the wetting and by reducing the soaking of the membrane of the membrane filter it is achieved that the air can pass through the membrane comparatively unimpeded. Such unimpeded passage of air, however, no longer is easily possible when the membrane of the membrane filter is strongly wetted and/or soaked with fluid.

By additionally omitting to apply a negative pressure on the hydraulic side, it is also achieved that a slow wetting of the hollow fiber membranes of the dialyzer is effected. It is also prevented that the air flows backwards from the blood circuit to the dialysate side and subsequently can possibly no longer be removed therefrom.

Furthermore, it is exploited that due to the opening of the second partial circuit towards the atmosphere the low back pressure existing in the second partial circuit considerably facilitates a passage of air through the membrane of the dialyzer.

In detail, the procedure can be as follows:

Before starting the method, the dialyzer is connected at least on the hydraulic side, as is already common practice. The blood-side connection, however, is not necessary for carrying out the method of the invention, but it is provided that the blood side is open to the atmosphere. In this way, it is prevented in particular that the dialysate-side charge is deteriorated, as in a filter closed on the blood side an increase in pressure occurs due to the air passing over on the blood side, which makes a further venting of the dialysate side impossible.

The extracorporeal blood circuit is opened to the surroundings. This can be effected for example in that a vent valve provided in the venous part of the extracorporeal blood circuit, e.g. in the region of or at a drip chamber or air trap, is opened.

Furthermore, it is e.g. conceivable and alternatively or additionally provided that a clamp element and an element comprising a hydrophobic membrane is provided as venting means. The clamp element for example can be a tubing part of the disposable which is provided with a manual clamp, whereby the disposable can be opened and closed towards the atmosphere.

There can also be provided a valve as vent valve and/or a valve which is designed such that it increases the compliance of a disposable tubing set of the blood treatment device, such as e.g. a single-needle valve. In this connection it is then conceivable in particular to open the single-needle valve when it is a blood treatment device for carrying out a single-needle method and a corresponding valve is provided.

Usually, the dialyzer already is connected with the tube system during the filling operation. In addition, this tube system is not open to the surroundings, since the two tube clamps are closed upon insertion and the valve for venting the venous chamber likewise is closed in the basic condition.

When filling in particular large dialyzers, an increase in pressure is observed in the extracorporeal blood circuit, since air passes over from the dialysate side to the blood side. If air is allowed to escape by opening the vent valve of the venous chamber, a distinctly improved hydraulic-side filling of the filter already can be seen. In some blood treatment devices it is also possible to produce a vacuum in the extracorporeal blood circuit. This can support the venting of the filter.

If air is allowed to escape from the extracorporeal blood circuit by opening e.g. a vent valve, the filling volume of the dialyzer significantly increases, as has been observed. To ensure that air can be separated via the membrane, filling the hydraulic side must be effected before filling the blood side, since a wetting of the membrane (no matter from which side) prevents a passage of air, and the pressure on this side of the membrane must be greater than on the other side. If the pressure on the side of the dialyzer to be filled is lower, air is sucked in and the charge is deteriorated distinctly.

The dialyzer first is filled on the hydraulic side, i.e. on the side of the first partial circuit. The filling routine has been modified such that the first five balancing chamber switching operations of the balancing chamber are performed via the dialyzer with a reduced and uniform dialysate flow rate. The same amounts to 500 ml/min. The air from the dialyzer is delivered into the secondary air separator.

It is taken into account that venting via the membrane only can be effected when capillary parts have not yet come into contact with dialysate. If all capillaries are wet at the end of the filling routine, air no longer can pass through the capillary membrane and the residual air must be rinsed out of the dialyzer. To prevent that all capillaries are drenched or soaked already at an early stage of the filling routine, the filling volumetric flow rate must have a rather uniform course.

In this phase, the hydraulic system operates in a balancing manner, i.e. equal volumes are delivered to and from the dialyzer. Thus, the displacement of air via the membrane only plays a subordinate role which is negligible.

The air flowing into the secondary air separator is detected there and normally separated by applying a negative pressure for sucking off the air. This procedure also is referred to as secondary air separation. In the present case of filling the dialyzer, however, the secondary air separation is inhibited, since applying a negative pressure in the balancing circuit leads to an undesired passage of air from the blood side to the dialysate side. This can be detected for example by abrupt pressure drops at the venous pressure sensor at the end of each balancing chamber switching operation.

To avoid idling of the secondary air separator, a transition to the filling program is effected after a certain number of balancing chamber switching operations. The balancing system here is opened at an additional valve. In the filling program, the balancing chamber delivers additional fluid into the balancing circuit. The driving force here is the charge pump which supplies a flow rate of about 1300 ml/min.

As can be demonstrated with the course of pressure in the extracorporeal blood circuit, air is shifted into the blood circuit during the first switching operations of the filling program and can lead there to a temporary increase in pressure e.g. because of the pressure drop at the hydrophobic membrane in the single-needle air port.

After a few switching operations, the dialyzer membrane is completely wetted or soaked and there is no further passage of air to the blood side. The remaining air is displaced by further filling switching operations, until fluid can be detected again.

Filling the dialyzer ends after a total of 15 switching operations. In principle, filling can of course also be terminated earlier in the case of smaller filters. From the sixth balancing chamber switching operation, filling is performed with the maximum flow rate (1000 ml/min) available from the machine during the normal switching operations, since the capillaries anyway are extensively wetted due to the high peak flow rate during the filling switching operations.

Further usable effects of the method described above also can consist in that an evaluation of the balancing chamber switching operations in the filling program is utilized to provide information on the dialysate-side filling volume of the filter. Together with the information of the blood-side filling volume (can be determined when filling the blood side), the dialyzer possibly can be determined on the machine side. Furthermore, an evaluation of the venous (and pre-filter) pressure pulses provides for detecting whether the blood tubings have been connected to the dialyzer without a leakage of fluid.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of rinsing and/or of filling a blood treatment device that includes a membrane filter, a first partial circuit and a second partial circuit, the first partial circuit and the second partial circuit being separated by the membrane filter in a semipermeable manner, and the first partial circuit being a dialysis circuit and the second partial circuit being an extracorporeal blood circuit, said method comprising:
   partly filling the first partial circuit with a fluid, such that the membrane filter is not being completely wetted by the fluid, while the second partial circuit is empty;
   providing, at least temporarily, within the second partial circuit, an opening to the atmosphere, or a vacuum thereto; and
   while the second partial circuit is open to the atmosphere or the vacuum is applied thereto, and with the first partial circuit partly filled and the membrane filter not completely wetted by the fluid, displacing air, via the membrane of the membrane filter, from the first partial circuit into the second partial circuit and therefrom via the opening or the vacuum,
   with, in the step of partly filling the first partial circuit, the first partial circuit being filled with the fluid with a first volumetric flow rate, the first volumetric flow rate not exceeding a specified threshold value, and at the threshold value, the fluid not yet completely wetting the membrane, and
   after the first partial circuit has been partly filled, in the step of displacing air from the first partial circuit into the second partial circuit via the membrane of the membrane filter, the fluid being delivered into the first partial circuit with a volumetric flow rate which is greater than the first volumetric flow rate.

2. The method according to claim 1, wherein in the step of partly filling the first partial circuit, the first partial circuit is at first partly filled in a balancing manner, wherein during the balancing filling equal volumes are delivered to and from the first partial circuit, and wherein a balancing chamber is used for the balancing filling, and
   after the first partial circuit has been partly filled, in the step of displacing air from the first partial circuit into the second partial circuit via the membrane of the membrane filter, a balancing system is opened and the balancing chamber delivers additional fluid into the first partial circuit.

3. The method according to claim 2, wherein while filling the membrane filter on the side of the first partial circuit, one or more operations are performed to effect the balancing with the balancing chamber.

4. The method according to claim 3, wherein after a specified number of the operations are performed, air is displaced from the first partial circuit into the second partial circuit via the membrane of the membrane filter.

5. The method according to claim 1, wherein the first volumetric flow rate does not exceed 500 ml/min, and/or the second volumetric flow rate exceeds 1000 ml/min.

6. The method according to claim 2, wherein the first partial circuit includes a secondary air separator into which air from the membrane filter is delivered during the step of partly filling the first partial circuit, without negative pressure being applied to the secondary air separator.

7. The method according to claim 1, wherein the membrane filter is arranged substantially vertically, the first partial circuit is filled with a flow direction of the liquid from a top to a bottom thereof, and the second partial circuit is filled with a flow direction of the liquid from the bottom to the top.

8. A blood treatment device comprising
   at least one membrane filter, at least one first partial circuit and at least one second partial circuit, at least one first pump for delivering a fluid in the first partial circuit and at least one second pump for delivering a fluid in the second partial circuit, the first partial circuit and the second partial circuit being separated by the membrane filter in a semipermeable manner, with the first partial circuit being a dialysis circuit and the second partial circuit being an extracorporeal blood circuit,
   a controller programmed to control the first pump and the second pump to rinse and/or fill the first partial circuit and the second partial circuit and the membrane filter in such a way that the first partial circuit is partly filled with the fluid and the membrane filter is not completely being wetted by the fluid, while the second partial circuit is still empty,
   the second partial circuit having, at least temporarily, an opening to the atmosphere or a vacuum created therein while air is displaced, with the first partial circuit being partly filled and the membrane not being completely wetted by the fluid, from the first partial circuit into the second partial circuit via the membrane of the membrane filter and therefrom via the opening or the vacuum,
   with the controller being programmed to control the first pump such that the first partial circuit is filled with a fluid with a first volumetric flow rate for partly filling the first partial circuit, with the first volumetric flow rate not exceeding a specified threshold value, and, at the threshold value the fluid not yet completely wetting the membrane, and
   the controller being programmed to control the first pump such that the first partial circuit is filled with a fluid with a second volumetric flow rate greater than the first volumetric flow rate for displacing air from the first partial circuit into the second partial circuit via the membrane of the membrane filter.

9. The blood treatment device according to claim 8, wherein the opening of the second partial circuit to the atmosphere is provided by a vent that includes a clamp and/or a valve.

10. The blood treatment device according to claim 8, further comprising at least one balancing chamber, and
    wherein the controller is programmed to control the first pump and the balancing chamber such that the first partial circuit is partly filled in a balancing manner by delivering equal volumes to and from the membrane filter by the first pump and by the balancing chamber.

11. The blood treatment device according to claim 8, wherein the first volumetric flow rate does not exceed 500 ml/min.

12. The blood treatment device according to claim 8, further comprising, in the first partial circuit, a secondary air separator into which the air from the membrane filter is delivered while partly filling the membrane filter on the side of the first partial circuit.

13. The blood treatment device according to claim 9, wherein the valve is at least one of a vent valve and a valve that increases the compliance of a disposable tubing set of the blood treatment device.

14. The blood treatment device according to claim 13, wherein the valve is a single-needle valve.

15. The method according to claim 1, wherein the air displaced from the first partial circuit into the second partial circuit is in a gaseous state as the air passes through the membrane.

* * * * *